US008119397B2

(12) United States Patent
Kato et al.

(10) Patent No.: US 8,119,397 B2
(45) Date of Patent: Feb. 21, 2012

(54) THERAPEUTIC AGENTS AND THERAPEUTIC METHODS FOR TREATING INJURED TISSUE

(75) Inventors: Yukio Kato, Hiroshima (JP); Masahiro Nishimura, Hiroshima (JP); Yoshie Ozaki, Hiroshima (JP); Koichiro Tsuji, Hiroshima (JP)

(73) Assignees: Two Cells Co., Ltd., Hiroshima (JP); Yukio Kato, Hiroshima (JP)

( * ) Notice: Subject to any disclaimer, the term of this patent is extended or adjusted under 35 U.S.C. 154(b) by 616 days.

(21) Appl. No.: 10/594,595

(22) PCT Filed: Mar. 31, 2005

(86) PCT No.: PCT/JP2005/006320
§ 371 (c)(1),
(2), (4) Date: Sep. 28, 2006

(87) PCT Pub. No.: WO2005/094888
PCT Pub. Date: Oct. 13, 2005

(65) Prior Publication Data
US 2008/0254019 A1    Oct. 16, 2008

(30) Foreign Application Priority Data
Mar. 31, 2004  (JP) ................. 2004-105890

(51) Int. Cl.
*C12N 5/00* (2006.01)
*A61K 38/16* (2006.01)
*C07K 1/00* (2006.01)
(52) U.S. Cl. .................. 435/325; 514/7.6; 530/350
(58) Field of Classification Search .................. 435/325; 514/7.6; 530/350
See application file for complete search history.

(56) References Cited

U.S. PATENT DOCUMENTS

| 6,132,214 | A | 10/2000 | Suhonen et al. | |
|---|---|---|---|---|
| 6,375,989 | B1* | 4/2002 | Badylak et al. | 424/551 |
| 7,456,262 | B2* | 11/2008 | Desnoyers et al. | 530/388.1 |
| 2002/0128444 | A1* | 9/2002 | Gingras et al. | |
| 2002/0132978 | A1* | 9/2002 | Gerber et al. | |
| 2004/0086507 | A1 | 5/2004 | Shitara et al. | |
| 2005/0159820 | A1 | 7/2005 | Yoshikawa et al. | |

FOREIGN PATENT DOCUMENTS

| JP | 2000-501966 A | 2/2000 |
|---|---|---|
| JP | 2001-089471 A | 4/2001 |
| JP | 2003-111831 A | 4/2003 |
| JP | 2003-325657 A | 11/2003 |
| JP | 2004-501608 | 1/2004 |
| WO | WO-01/70174 A2 | 9/2001 |
| WO | WO-02/33094 A1 | 4/2002 |
| WO | WO-03/013588 A1 | 2/2003 |
| WO | WO-03/015802 A1 | 2/2003 |
| WO | WO 2004/007697 A2 | 1/2004 |

OTHER PUBLICATIONS

Fiedler et al., 2002, Journal of Cellular Biochemistry, vol. 87, p. 305-312.*
Deonarain, 1998, Expert Opin. Ther. Pat., vol. 8, pp. 53-69.*
Verma et al., Sep. 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Hamman et al., 2005, Biodrugs, vol. 19, No. 3, p. 165-177.*
Torchilin et al., 2003, DDT, vol. 8, No. 6, p. 259-266.*
Kaye et al., 1990, Proc. Natl. Acad. Sci. USA, vol. 87, pp. 6922-6926.*
Davis, C. G., 1990, The New Biologist, vol. 2, No. 5, p. 410-419.*
Skolnick et al., 2000, Trends in Biotech, vol. 18, p. 34-39.*
Dabbagh et al., 1998, Thrombosis and Haemostasis, vol. 79, No. 2, pp. 405, Summary only.*
Sano et al., 2003, Advanced Drug Delivery Reviews, vol. 55, p. 1651-1677.*
Antonella, Journal of cell Science, 2003, vol. 117, No. 7, pp. 1151-1160.
Ying, Biochemical and Biophysical Research Communications, 2003, vol. 308, pp. 126-132.
Ogushi, Experimental Medicine, 2003, vol. 21, No. 8, pp. 161-165.
Shingo, Experimental Medicine, 2003, vol. 21, No. 8, pp. 140-147.
Iniwa, Experimental Medicine, 2003, vol. 21, No. 8, pp. 154-160.
Sugi, Developmental Biology, 2003, vol. 258, pp. 252-263.
Balk, Life Science, 1984, vol. 35, No. 4, pp. 335-346.
Moadsiri, Blood, 2002, vol. 100, No. 11, p. Abstract No. 2059.
Mahmood A et al., Neurosurgery 2001;49:1196-203; discussion 203-4.
Lu D et al., Cell Transplantation 2002;11:275-81.
Lu D et al., J Neurotrauma 2001;18:813-9.
Li Y et al., J Cereb Blood Flow Metab 2000;20:1311-9.
Chen J et al., Stroke 2001;32:1005-11.
Devine MJ et al., J Orthop Res 2002;20:1232-9.
Yu J et al., Biochem Biophys Res Commun 2001;697-700.
Hirschi KK et al., Circ Res 1999;84:298-305.
Kohno M et al., J Am Soc Nephrol 1999;10:2495-502.
Kondo H et al., Biochem Biophys Res Commun 2000;272:648-52.
Shono T et al., Exp Cell Res 2001;264:275-83.
Mayr-Wohlfart U et al., Bone 2002;30:472-7.
Liu J et al., Oncogene 1999;124:547-55.
Chen P et al, J Cell Biol 1994;124:547-55.
Kawahara E et al., Exp Cell Res 2002;272:84-91.
Takemura T et al., J Biol Chem 1997;272:31036-42.
Barnard JA et al., J Biol Chem 1994;269:22817-22.
Wilson SE et al., Exp Eye Res 1996;62:325-7.
Schultz G et al., J Cell Biochem 1991;45:346-52.
Cha D et al., Invest Dermatol 1996;106:590-7.

(Continued)

*Primary Examiner* — Shin-Lin Chen
(74) *Attorney, Agent, or Firm* — Birch, Stewart, Kolasch and Birch, LLP

(57) ABSTRACT

This invention provides therapeutic agents, transplants and therapeutic methods that can enhance the regeneration of injured tissue. This invention relates to agents, transplants and therapeutic methods for enhancing the migration and accumulation of mesenchymal stem cells in injured tissues and/or suppressing the diffusion of mesenchymal stem cells from injured tissues.

2 Claims, 5 Drawing Sheets

OTHER PUBLICATIONS

Crouch MF et al., J Cell Biol 2001;152:263-73.
Kaufmann R et al., Cancer Lett 2002;180:183-90.
Ikeda M et al., Arterioscler Thromb Vasc Biol 1997;17:731-6.
Pedram A et al., Endocrinology 2001;142:1578-86.
Kume K et al., J Histochem Cytochem 2002;50:159 69.
Gordeladze JO et al., J Cell Biochem 2002;85:825-36.
European Search Report for EP 05 72 7997 dated Nov. 18, 2009, Two Cells Co., Ltd.
Akita, et al., Wound Rep Reg, (2004), vol. 12, pp. 252-259.
Ozaki, Stem Cells Development, (2007), vol. 16, pp. 119-129.
Bensaid, W. et al., "A Biodegradable Fibrin Scaffold for Mesenchymal Stem Cell Transplantation", Biomaterials, vol. 24, No. 14, pp. 2497-2502, 2003.
Kato, Y. et al., "I. Regenerative Medicine of Bone, Cartilage and Periodontal Tissues by Transplantation of Autologous Mesenchymal Stem Cells", The Bone, vol. 17, No. 1, pp. 17-20, 2003.
Kato, Y. et al., "Mesenchymal Stem Cells for Regeneration Medicine", The Journal of Hiroshima Dental Association, vol. 30, No. 1, pp. 1-9, 2002.
Azuma, H., "Pathogenesis of hereditary hemorrhagic telangiectasia", Igaku no Ayumi, Ishiyaku Publishers, Inc., vol. 191, No. 5, p. 523-528, 1999.
Japanese Office Action for JP Patent Appl. No. 2006-511809 based on PCT/JP2005/006320, issued Mar. 31, 2011.
Liu J et al., Oncogene 1999; 18:6700-6.

* cited by examiner

THERAPEUTIC AGENTS AND THERAPEUTIC METHODS FOR TREATING INJURED TISSUE

TECHNICAL FIELD

This invention relates to an agent, a transplant and a therapeutic method for enhancing the migration and accumulation of mesenchymal stem cells in injured tissue and/or suppressing the diffusion of mesenchymal stem cells from injured tissue. More particularly, this invention relates to an agent and a transplant containing mesenchymal stem cell migration-enhancing factors as well as therapeutic methods using such mesenchymal stem cell migration-enhancing factors that are effective for tissue regeneration therapy in osteoarthritis, bone fracture, loss of alveolar bone or jaw bone, cerebral infarction, myocardial infarction, lower limb ischemia, etc.

BACKGROUND ART

For living tissue regeneration, various methods including the administration of pharmaceuticals and surgical operations have heretofore been attempted but no agents or therapeutic methods have proved fully effective in regeneration of injured or defective tissue. In recent years, a large number of reports have been published on the migration and accumulation of stem cells to the injured sites of tissue. It has been reported that when mesenchymal stem cells (hereinafter sometimes abbreviated to MSCs) or cells in umbilical cord blood are injected to traumatic brain injury intravenously or MSCs are injected by intraarterial route, the injected cells accumulate in the injured brain (Mahmood A et al., Neurosurgery 2001;49: 1196-203; discussion 203-4; Lu D et al., Cell Transplantation 2002;11:275-81; Lu D et al., J Neurotrauma 2001;18:813-9). It has also been reported that intrastriatal transplantation of bone marrow nonhematopoietic cells improves functional recovery in mice with brain injury (Li Y et al., J Cereb Blood Flow Metab 2000;20:1311-9). In addition, it was found that intravenous infusion of MSCs in model rats with middle cerebral artery occlusion enabled them to recover their neurological severity scores compared with untreated groups, with some rats being recognized to show differentiation of the transplanted MSCs into neurons (Chen J et al., Stroke 2001; 32:1005-11).

It has also been reported that when bone marrow cells are injected intravenously into an experimentally induced fractures, the injected bone marrow cells "home" to the bone marrow and localize to fracture callus in a mouse (Devine M J et al., J Orthop Res 2002;20:1232-9). However, it has not yet become clear how the cells recognize an injured site in the process of their migration and accumulation.

Extensive in vitro reviews have been made to date about individual migration and accumulation factors for various cells. PDGF (platelet-derived growth factor) BB is known as a paracrine-like migration and accumulation factor for various kinds of adhesive cells (Yu J et al., Biochem Biophys Res Commun 2001;282:697-700). PDGF-BB is an especially potent migration and accumulation factor for endothelial cells or mesangial cells (Hirschi K K et al., Circ Res 1999; 84:298-305; Kohno M et al., J Am Soc Nephrol 1999;10: 2495-502). FGF2 (fibroblast growth factor-2) is known as an autocrine-like migration and accumulation factor (Kondo H et al., Biochem Biophys Res Commun 2000;272:648-52) and its migration and accumulation ability and mechanism in endothelial cells, osteoblasts, fetal fibroblasts, etc. are being reviewed (Shono T et al., Exp Cell Res 2001;264:275-83; Mayr-Wohlfart U et al., Bone 2002;30:472-7; Liu J et al., Oncogene 1999;18:6700-6). EGF (epidermal growth factor) is also reported as a migration and accumulation factor for several cells (Chen P et al., J Cell Biol 1994;124:547-55). Recently, the EGF's action mechanism in the migration and accumulation of cancer cells is also being reviewed (Kawahara E et al., Exp Cell Res 2002;272:84-91). HB-EGF (heparin-binding epidermal growth factor) which is a member of EGF family has been reported to enhance the survival, proliferation, as well as migration and accumulation of epidermal cells (Takemura T et al., J Biol Chem 1997;272:31036-42; Barnard J A et al., J Biol Chem 1994;269:22817-22; Wilson SE et al., Exp Eye Res 1996;62:325-7) but no review has been made except for the epidermal cells. TGF-α has been reported to have approximately 30-40% homology with EGF and as taking part in tissue repair via the EGF receptor (Schultz G et al., J Cell Biochem 1991;45:346-52). TGF-α has been reported to be mainly responsible for the proliferation as well as migration and accumulation of keratinocytes (Cha D et al., J Invest Dermatol 1996;106:590-7) but no reports have been made concerning other cells.

Thrombin is known as an enzyme that coagulates blood by converting fibrinogen to fibrin, and it has recently been reported as enhancing the proliferation as well as migration and accumulation of Swiss 3T3 cells by inducing the clustering of their EGF receptors (Crouch M F et al., J Cell Biol 2001;152:263-73). It has also been reported as enhancing the migration and accumulation of human renal cancer cells (Kaufmann R et al., Cancer Lett 2002;180:183-90). Atrial natriuretic peptide (ANP) is a peptide composed of 28 amino acids that are synthesized in the heart and occurs in circulating blood. ANP has a potent diuresis and vasodilation effect, vascular smooth muscle relaxation effect, a rennin-angiotensin system suppressing effect, a sympathetic nerve suppressing effect, and the like, and it has been reported that ANP suppresses the migration and accumulation of endothelial cells, as exemplified by suppression of the PDGF mediated migration and accumulation of vascular smooth muscle cells (Ikeda M et al., Arterioscler Thromb Vasc Biol 1997;17:731-6) and in the case of suppressing the VEGF's mediated migration and accumulation of endovascular cells (Pedram A et al., Endocrinology 2001;142:1578-86). Leptin, a 16-kD circulating protein secreted mainly by adipose tissue, is a product of the obese gene. Leptin has been reported to enhance the proliferation, migration and accumulation, tube formation, etc. of human endothelial cells in vitro and it has been reported that leptin probably induces endochondral ossification by inducing angiogenesis (Kume K et al., J Histochem Cytochem 2002;50:159 69). It has also been reported that leptin enhances collagen synthesis and mineralization of iliac osteoblasts (Gordeladze J O et al., J Cell Biochem 2002;85: 825-36). However, nothing is known about the migration ability of those factors with respect to MSCs.

DISCLOSURE OF THE INVENTION

Problems to be Solved by the Invention

As described above, it has been reported that the accumulation of MSCs at injured sites has the possibility of enhancing the regeneration of injured tissue but nothing is known about substances that can allow MSCs to accumulate specifically at injured sites or methods and agents that use such substances to enhance the healing of injured tissue.

An object of the present invention is to provide therapeutic agents, transplants and therapeutic methods that may enhance the regeneration of injured tissue in osteoarthritis, bone fracture, loss of alveolar bone or jaw bone, cerebral infarction, myocardial infarction, lower limb ischemia, etc. by using substances that allow MSCs to accumulate specifically at injured sites or which prevent diffusion of MSCs.

Means for Solving the Problems

The inventors made intensive studies with a view to solving the aforementioned problems; as a result, they found a chemotactic factor that would enhance the migration and accumulation of MSCs and which, surprisingly enough, would also enhance the proliferation of MSCs; they learned that agents and transplants that contained those chemotactic factors were effective in treatments for living tissue regeneration. The present invention has been accomplished on the basis of these findings.

According to the present invention, there is provided an agent or a transplant for enhancing the migration and accumulation of mesenchymal stem cells in an injured tissue and/or suppressing the diffusion of mesenchymal stem cells from an injured tissue.

The agent or transplant preferably contains a mesenchymal stem cell migration-enhancing factor, and more preferably they contain a mesenchymal stem cell migration-enhancing factor that enhances the proliferation of mesenchymal stem cells.

The agent or transplant is preferably used in regeneration therapy and it is particularly preferred to use it in a regeneration (therapy) of injured tissue resulting from osteoarthritis, bone fracture, loss of alveolar bone or jaw bone, cerebral infarction, myocardial infarction, or lower limb ischemia.

The mesenchymal stem cell migration-enhancing factor contained in the agent or transplant is preferably selected from the group consisting of EGF (epidermal growth factor), HB-EGF (heparin-binding epidermal growth factor), TGF-α, thrombin, PDGF (platelet-derived growth factor), FGF (fibroblast growth factor), hyaluronic acid, IGF (insulin-like growth factor), and HGF (hepatocyte growth factor).

The agent may be administered simultaneously with, or continuously to, or separately from mesenchymal stem cells.

The transplant may be administered simultaneously with, or continuously to, or separately from mesenchymal stem cells.

According to another aspect of the present invention, there is provided a method of regeneration therapy of injured tissue which comprises either enhancing the migration and accumulation of mesenchymal stem cells in the injured tissue and/or suppressing the diffusion of mesenchymal stem cells from the injured tissue.

The method preferably comprises administering a mesenchymal stem cell migration-enhancing factor.

In the method, the injured tissue is preferably a result of osteoarthritis, bone fracture, loss of alveolar bone or jaw bone, cerebral infarction, myocardial infarction, or lower limb ischemia.

The mesenchymal stem cell migration-enhancing factor administered in the method is preferably selected from the group consisting of EGF, HB-EGF, TGF-α, thrombin, PDGF, FGF, hyaluronic acid, IGF, and HGF.

In the method, the mesenchymal stem cell migration-enhancing factor is preferably administered topically to the injured tissue, and it is particularly preferred to administer it by injection or apply it over the injured tissue.

In the method, mesenchymal stem cells may be administered to the injured tissue and/or its periphery simultaneously with, or continuously to, or separately from the administration of the mesenchymal stem cell migration-enhancing factor.

In still another aspect, the present invention relates to the use of the mesenchymal stem cell migration-enhancing factor for manufacturing an agent or a transplant for enhancing the migration and accumulation of mesenchymal stem cells in an injured tissue and/or suppressing the diffusion of mesenchymal stem cells from an injured tissue.

Effect of the Invention

According to the present invention, there are provided an agent, a transplant, a therapeutic method and the like that are effective in a regeneration therapy of injured tissues.

BRIEF DESCRIPTION OF THE DRAWINGS

FIG. 3 shows by graphs the effect of PDGF-BB in stimulating the migration and accumulation of human ilium-derived MSCs (ILIUM MSC) and human jaw bone-derived MSCs (ALVEOLAR BONE MSC); the crosshatched bar graphs show CI for PDGF-BB at a final concentration of 10 ng/mL and the solid bar graphs show CI for a zero concentration of PDGF-BB.

FIG. 5 shows by electrophoretograms the effects of PDGF-BB localized in rat's calf, in stimulating the migration and accumulation of rat-derived MSCs.

FIG. 6 shows by a graph the concentrations of GFP bands in FIG. 5 as corrected by the concentrations of GAPDH bands.

BEST MODE FOR CARRYING OUT THE INVENTION

Figure 1:
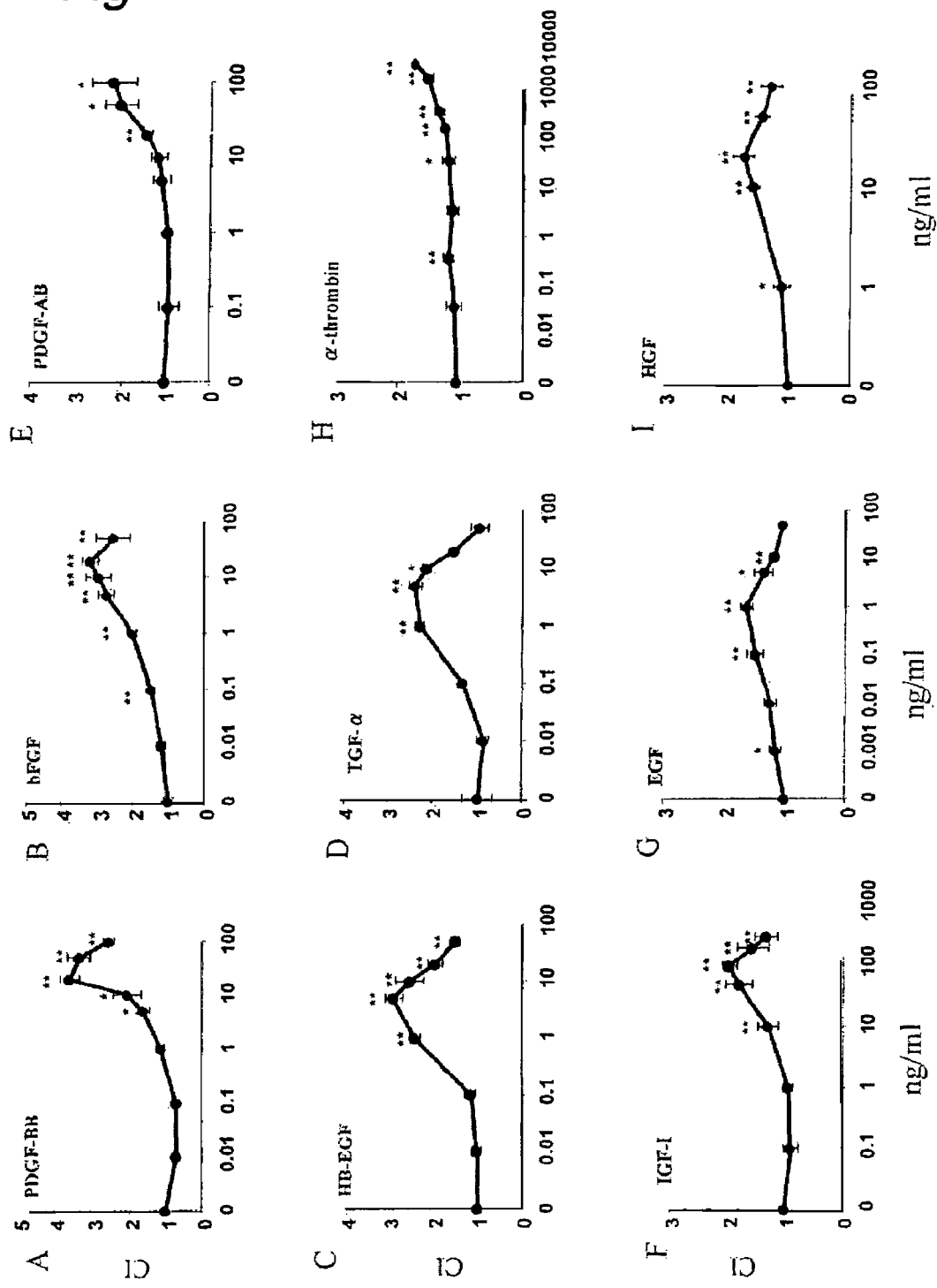
[FIG. 1] The graphs A, B, C, D, E, F, G, H and I in FIG. 1 show dose-response curves for the effects of PDGF-BB, b-FGF, HB-EGF, TGF-α, PDGF AB, IGF-I, EGF, α-thrombin and HGF, respectively, in stimulating the migration and accumulation of rabbit-derived MSCs.

In the present invention, the term "mesenchymal stem cells" refers to tissue stem cells that have multipotency in differentiation to bone (osteoblast), cartilage (chondrocyte), fat (adipocyte), blood vessel, nerve, etc.

In the present invention, the expression "enhancing the migration and accumulation of mesenchymal stem cells in an injured tissue and/or suppressing the diffusion of mesenchymal stem cells from an injured tissue" means that either enhancement of the migration and accumulation of mesenchymal stem cells in an injured tissue, or suppression of the diffusion of mesenchymal stem cells from an injured tissue, or both are effected.

In the present invention, the term "mesenchymal stem cell migration-enhancing factor" refers to a factor that enhances the migration and accumulation of mesenchymal stem cells. Further, in the present invention, the term "mesenchymal stem cell migration-enhancing factor that enhances the proliferation of mesenchymal stem cells" refers to a factor that enhances not only the migration and accumulation of mesenchymal stem cells but also the proliferation of mesenchymal stem cells.

In the present invention, the term "injured tissue" means tissues that have suffered injuries (including destruction and loss of tissues) resulting from osteoarthritis, bone fracture, loss of alveolar bone or jaw bone, cerebral infarction, myocardial infarction, or lower limb ischemia. It also means skin, ligament, meniscus, tendon, liver, kidney, esophagus, stomach, lung, hair and all other tissues that suffered injury.

In the present invention, the term "regeneration of injured tissue" means reconstruction or reproduction of an injured tissue. In osteoarthritis, for example, this term may refer to the recovery of joint cartilage to a state in which it is smooth with the same thickness as the surrounding cartilage, etc. In a bone fracture, for example, the term may refer to the recovery of cortical bone to a state in which it binds continuously to the surrounding bone with the same thickness as the latter, etc. In a loss of alveolar bone, for example, the term may refer to a phenomenon in which the height of an alveolar bone that supports a tooth absorbed due to periodontal disease, bruxism, occlusal trauma, orthodontic therapy, etc. recovers to a level approaching the cement-enamel border or in which the level of the alveolar bone recovers to such a state that the tooth movement is within a clinically tolerable range. In cerebral infarction, for example, the term may refer to recovery, which may be partial, of the brain functions that were lost by infarction. In myocardial infarction, for example, the term may refer to recovery, which may be partial, of the myocardial functions that suffered the infarction. In lower limb ischemia, for example, the term may refer to the recovery of endovascular functions of peripheral tissue on account of blood vessels regeneration.

In the present invention, the term "regeneration therapy of injured tissue" describes a concept that includes not only a treatment for enhancing regeneration of an injured tissue but also a case where the exacerbation of an existing injury is prevented or the degree of such exacerbation is reduced as compared with a case where the agent or the therapeutic method of the subject application is not applied.

In the present invention, the term "transplant" means one which involves the MSC migration-enhancing factor and a carrier that serves as a scaffold for causing the factor to act at a specified concentration on a specified site (e.g. a site in the living body such as an injured site of a joint, a transcervical fractured site or an alveolar bone or jaw bone missing site).

The MSC migration-enhancing factor to be used in the present invention may be artificially produced by recombinant gene technology or chemical synthesis or it may be of a native type.

The route for administration of the drug of the present invention is not limited in any particular way and it may be intravenous administration, intramuscular administration, intraperitoneal administration, transcutaneous administration, administration via the airway, intracutaneous administration, subcutaneous administration, or the like.

The agent of the present invention may also be administered topically by injection or the like. For example, it may be injected into an injured joint, a fractured site, an alveolar bone or jaw bone missing site, an infarct site, an ischemic site or their periphery, or the like.

The agent of the present invention may be administered topically as a medicine for external application. For example, in the case of alveolar bone absorption due to periodontal disease, bruxism, occlusal trauma, orthodontic therapy, etc., the agent, being filled into a syringe or the like, may be directly injected into a periodontal pocket. It is also possible to administer the drug to a missing part of the periodontium during periodontal surgical therapy. In this case, in order to ensure that the therapeutic agent of the present invention will exhibit its effect for a prolonged period of time at a constant concentration, it is also preferred to have it absorbed by a sheet or sponge before use. It is preferably administered after removing the infected periodontium. It may be administered topically to an alveolar bone or jaw bone missing part after extracting a cyst or a tumor.

Consider, for example, the case of a bone fracture. If a bone fragment has been separated, it is first restored by a conventional method of redintegration and is fixed into position before the agent of the present invention is administered by injection into the fractured site; if the bone fragment has not been fully separated (as in the case where a crack has occurred in the bone) and there is no need for redintegration, it may be fixed as it is before the agent of the present invention is administered by injection into the fractured site.

If the agent of the present invention is to be used, it is preferably formulated into a suitable dosage form by an ordinary pharmaceutical formulation procedure using a pharmaceutically acceptable carrier, diluent or the like. Exemplary dosage forms include medicines for external application such as ointment, cream and lotion, as well as injections based on aqueous solvents. The agent can also be used in a powder dosage form after dissolving it in a solubilizing liquid such as purified water just prior to use. Alternatively, the MSC migration-enhancing factor may be mixed with a carrier such as gelatin, PLGA [poly(lactic glycolic acid)], PGA [(poly(glycolic acid)], PLA [poly(lactic acid)], hydroxyapatite, or β-TCP (β-tricalcium phosphate) and then freeze-dried or otherwise treated to make an applicable drug. Alternatively, it may be used in admixture with blocks, granules or other shapes of calcium phosphate filler or hydroxyapatite filler. Other dosage forms include tablets, granules, subtilized granules, capsules, powders, solutions, suspensions, emulsions, agents to be absorbed through the skin, inhalants, suppositories, etc.

The dose and the interval between administrations vary with the kind of MSC migration-enhancing factor to be used, the route of administration, the dosage form, the position of an injured tissue, its scope, degree, severity of the injury, the age and sex of the subject to whom the agent is to be administered, and other factors; in topical administration, it is usually preferred that the dose is in the range of 1 pg to 1 mg, more preferably in the range of 1000 pg to 100 μg, and most preferably in the range of 10 ng to 1 μg, per site as calculated for the MSC migration-enhancing factor. Generally speaking, injections for topical administration need to be administered in smaller doses than drugs for external application. The therapeutic agent of the present invention may be administered for about one to five weeks (say, about three weeks) at a frequency of once to four times a week (say, once every two days). If desired, MSCs may be topically administered to an injured site or its periphery simultaneously with the administration of the therapeutic agent of the present invention, or continuously before or after the administration of the latter, or separately with a gap of a certain period of time before or after the administration of the latter; in these cases, the frequency of administration of the therapeutic agent of the present invention may sometimes be reduced.

The transplant of the present invention preferably contains the MSC migration-enhancing factor in an amount of 1 pg to 1 mg (more preferably from 1000 pg to 100 μg, and most preferably from 10 ng to 1 μg) per cubic centimeter of the transplant. If desired, MSCs may be topically administered to an injured site or its periphery simultaneously with the transplantation of the transplant of the present invention, or continuously before or after the transplantation of the latter, or separately with a gap of a certain period of time before or after the transplantation of the latter.

Unless its efficacy is not impaired, the therapeutic agent or transplant of the present invention may be used in combination with other agents. For example, they may be used in combination with antibiotics (e.g., penicillin and streptomycin) or antifungal agents (e.g., amphotericin) that are effective for preventing infection; alternatively, they may be used in combination with anti-inflammatory agents such as steroids (e.g., dexamethasone). If desired, MSCs may be topically administered to an injured site together with the therapeutic agent or transplant of the present invention.

The carrier to be combined with the MSC migration-enhancing factor in the transplant of the present invention may be any material that can maintain the MSC migration-enhancing factor at the site to which it was transplanted, that does no harm to the living body, and that will not interfere with the action of the MSC migration-enhancing factor. For example, a porous sheet or sponge can be used. Biodegradable protein materials (collagen, gelatin, albumin, and platelet-rich plasma (PRP)) and tissue absorbing materials (polyglycolic acid (PGA), polylactic acid (PLA), poly(lactic acid-co-glycolic acid) (PLGA), hyaluronic acid (HA), and tricalcium phosphate (TCP)) are preferred since they do not have to be extracted at a later time. Examples include TERUPLUG (trade name of TERUMO CORPORATION), GC Membrane (trade name of GC Co., Ltd.) and Osferion (trade name of OLYMPUS CORPORATION). Alternatively, the MSC migration-enhancing factor may be mixed with conventional bone fillers [e.g., calcium phosphate fillers and hydroxyapatite fillers such as APACERAM (trade name of PENTAX Corporation)] to prepare transplants, and bone fillers in granular or block form are preferably used.

The present invention is described below in greater detail with reference to the following examples, to which the present invention is by no means limited.

EXAMPLES

Example 1

(Cell Cultivation)

MSC isolation was performed following the method of Tsutsumi et al. (Tsutsumi S, B. B. R. C. 2001;288:413-419). To be specific, three 4-week old male Japanese white rabbits (SPF, produced by KITAYAMA LABES CO., LTD.) were administered intraperitoneally with an excess amount of the anesthetic nembutal, slaughtered, had the thigh bone and the shank removed from both sides, and also had their epiphyses cut off; the bone marrow present in those bones was flushed out using 21-G needles (TERUMO) in about 20 mL, per bone, with Dulbecco's modified Eagle medium (Sigma) (containing penicillin G at a final concentration of 100 units/mL, streptomycin sulfate at a final concentration of 100 μg/mL, amphotericin B (GIBCO) at a final concentration of 0.0085%, and 10% fetal calf serum) and the suspension was separated into individual bone marrow cells using a pipette. A Petri dish (175 cm$^2$; Falcon) containing the above-described Dulbecco's modified Eagle medium was sown with all bone marrow fluids from the thigh bone and the shank for one leg and the cells (MSCs) adhering to the bottom of the dish were kept cultured in the same medium (37° C., 5% $CO_2$, 95% air); when a colony formed (on day 7), the cells were subcultured on a new Petri dish at a cell density of 5000 cells/cm$^2$.

(Cell Migration Test)

The following 22 test substances were evaluated for their effect of stimulating the migration and accumulation of the rabbit-derived MSCs prepared in the above step: PDGF-BB (product of Genzyme Techne), bFGF (basic fibroblast growth factor, product of KAKEN PHARMACEUTICAL CO., LTD.), HB-EGF (product of Sigma), TGF-α (product of DIACLONE Research), PDGF-AB (product of Genzyme Techne), IGF-I (insulin-like growth factor-I, product of BD Biosciences), EGF (product of Pepro Tech EC), α-thrombin (product of Enzyme Research Laboratories), HGF (product of Pepro Tech EC), TGF-β1 (product of Pepro Tech EC), TGF-β3 (product of Pepro Tech EC), IL-2 (product of Pepro Tech EC), SCGF-α (stem cell growth factor-α, product of Pepro Tech EC), SCF (stem cell factor, product of Pepro Tech EC), SDF-1α (stromal cell-derived factor-1α, product of Pepro Tech EC), leptin (product of DIACLONE Research), BDNF (brain-derived neurotrophic factor, product of Wako Pure Chemical Industries, Ltd.), NGF-β (nerve growth factor-β, product of Sigma), NT-3 (neurotrophin-3, product of Sigma), ANP (product of Biogenesis), hyaluronic acid (polymer, product of DENKI KAGAKU KOGYO), and PDGF-AA (product of Pepro Tech EC).

The rabbit-derived MSCs were suspended in a serum-free Dulbecco's modified Eagle medium (containing penicillin G at a final concentration of 100 units/mL, streptomycin sulfate at a final concentration of 100 μg/mL, and amphotericin B at a final concentration of 0.0085%) at a cell density of 1×10$^6$ cells/mL so as to prepare an MSC sample solution. The respective test substances were dissolved in the above-mentioned serum-free Dulbecco's modified Eagle medium to give the final concentrations shown in FIGS. 1 and 2 so as to prepare solutions of the test substances. Each of the wells on a 96-well Boyden's chamber (Neuro Probe Inc.) was divided into an upper part and a lower part by means of a polycarbonate filter (pore size: 8 μm, Neuro Probe Inc.) that had been coated overnight with 0.01% type 1 collagen on both sides at 4° C. A 25-μL portion of each test substance solution was put into the lower layer of the filter on each well and a 50-μL portion of the MSC sample solution was put into the upper layer of the filter on the well (5×10$^4$ cells/well). Test was conducted using four wells for each concentration of one test substance. Used as a control was a well in which 25 μL of a medium that did not contain any test substance was solely placed in the lower layer of the filter whereas 50 μL of the MSC sample solution was solely placed in the upper layer of the filter.

After incubating the Boyden's chamber in 5% $CO_2$ at 37° C. for 6 hours, the filter was removed and the migrating and accumulating rabbit-derived MSCs were fixed with methanol and stained with Diff-Quik (product of INTERNATIONAL REAGENTS). The cells on the top surface of the filter were mechanically wiped with KIM-WIPE and the absorbance at 605 nm of the Diff-Quik stained cells under the filter was measured with Immuno Mini NJ2300 (Nunc). From the obtained data, dose-response curves were constructed for the respective test substances.

(Results)

Figure 2:
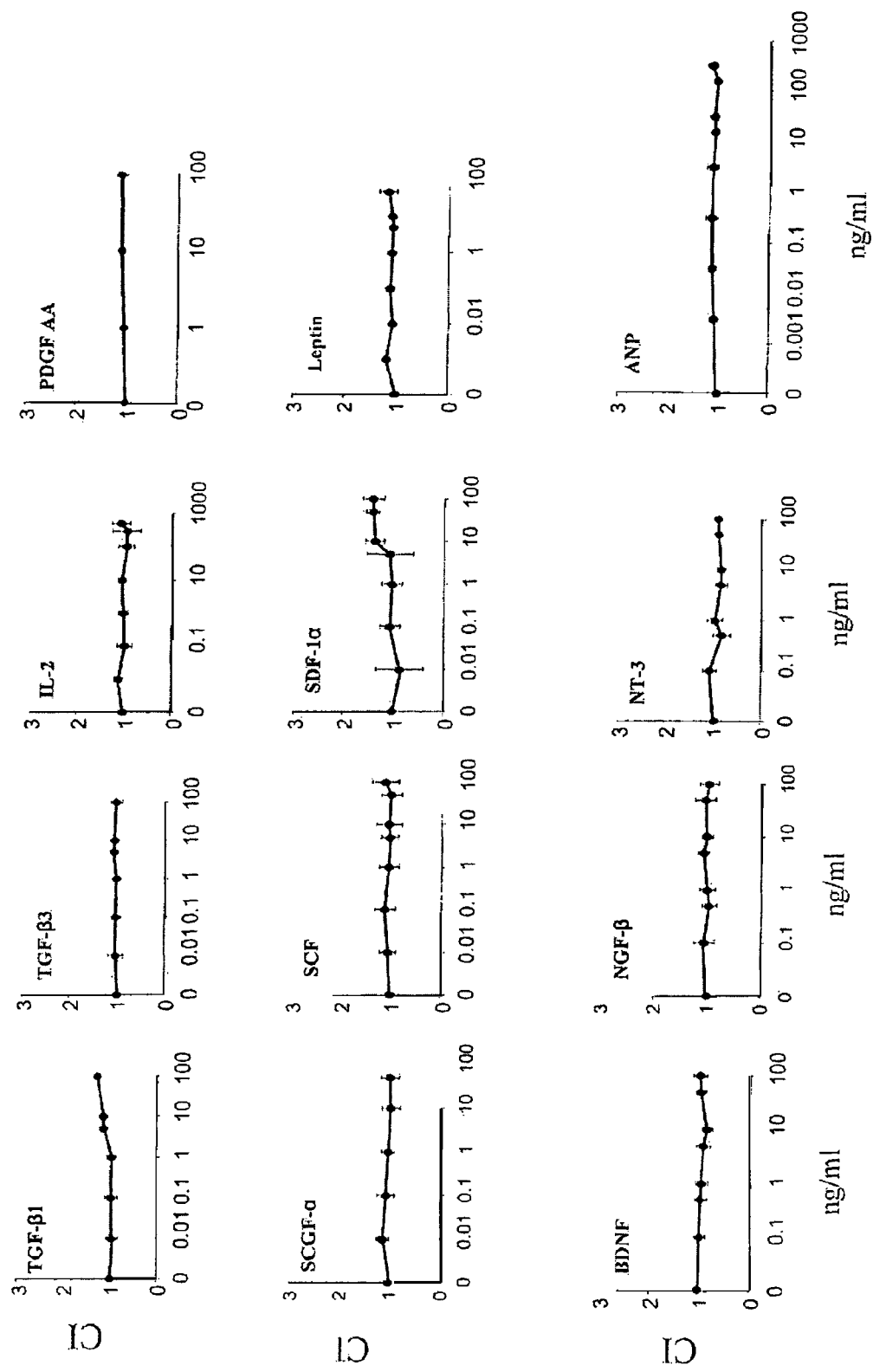
[FIG. 2] The graphs in FIG. 2 show dose-response curves for the effects of TGF-β1, TGF-β3, IL-2, PDGF-AA, SCGF-α, SCF, SDF-1α, leptin, BDNF, NGF-β, NT-3 and ANP, respectively in stimulating the migration and accumulation of rabbit-derived MSCs.

The results are shown by graphs in FIGS. 1 and 2. The vertical axis plots the chemotaxis index (CI), namely, the absorbance of cells that moved to beneath the filter in a well filled with a test substance as divided by the absorbance of cells that moved to beneath the filter in the control well. Statistical testing was done by t-test. In each of the graphs in FIG. 1, * represents $p<0.05$ and ** represents $<0.01$. In each of the graphs in FIGS. 1 and 2, the vertical bars represent mean±SD.

As is clear from the respective graphs, each of PDGF-BB, bFGF, HB-EGF, TGF-α, PDGF-AB, IGF-I, EGF, α-thrombin and HGF significantly enhanced the migration and accumulation of the rabbit-derived MSCs; on the other hand, no significant effect was recognized in TGF-β1, TGF-β3, IL-2, SCGF-α, SCF, SDF-1α, leptin, BDNF, NGF-β, NT-3, ANP or PDGF-AA. Although not shown, the high molecular weight hyaluronic acid significantly enhanced the migration and accumulation of the rabbit-derived MSCs when it was used in amounts ranging from about 10 μg/mL to 5 mg/mL.

Example 2

Using 1F1061 cells and 1F2155 cells (human ilium-derived MSCs purchased from Cambrex) and Kt-10 cells and Kt-11 cells (human jaw bone-derived MSCs), a cell migration test was conducted as in Example 1.

The 1F1061 cells and 1F2155 cells had already been confirmed to be positive in CD29, 44, 105 and 106 but negative in CD14, 34 and 45, as well as to be potent in differentiation to osteoblast, chondrocyte and adipocyte.

The Kt-10 cells and Kt-11 cells were obtained by the following procedure in Hiroshima University Dental Hospital from an excess bone marrow fluid that resulted from extracting refractory teeth and excising the jaw bone: the bone marrow fluid was suspended in a Dulbecco's modified Eagle medium containing 200 U/mL of heparin (assigned the Ethics Committee Approval No. 2) and allowed to grow on a Petri dish as in Example 1. The Kt-10 cells and Kt-11 cells had also been confirmed to be potent in differentiation to osteoblast, chondrocyte and adipocyte.

(Cell Migration Test)

The effects of PDGF-BB, HB-EGF, TGF-α, PDGF-AB, IGF-I and EGF in stimulating the migration and accumulation of the above-described human ilium-derived MSCs and human jaw bone-derived MSCs were evaluated as in Example 1.

Figure 3:
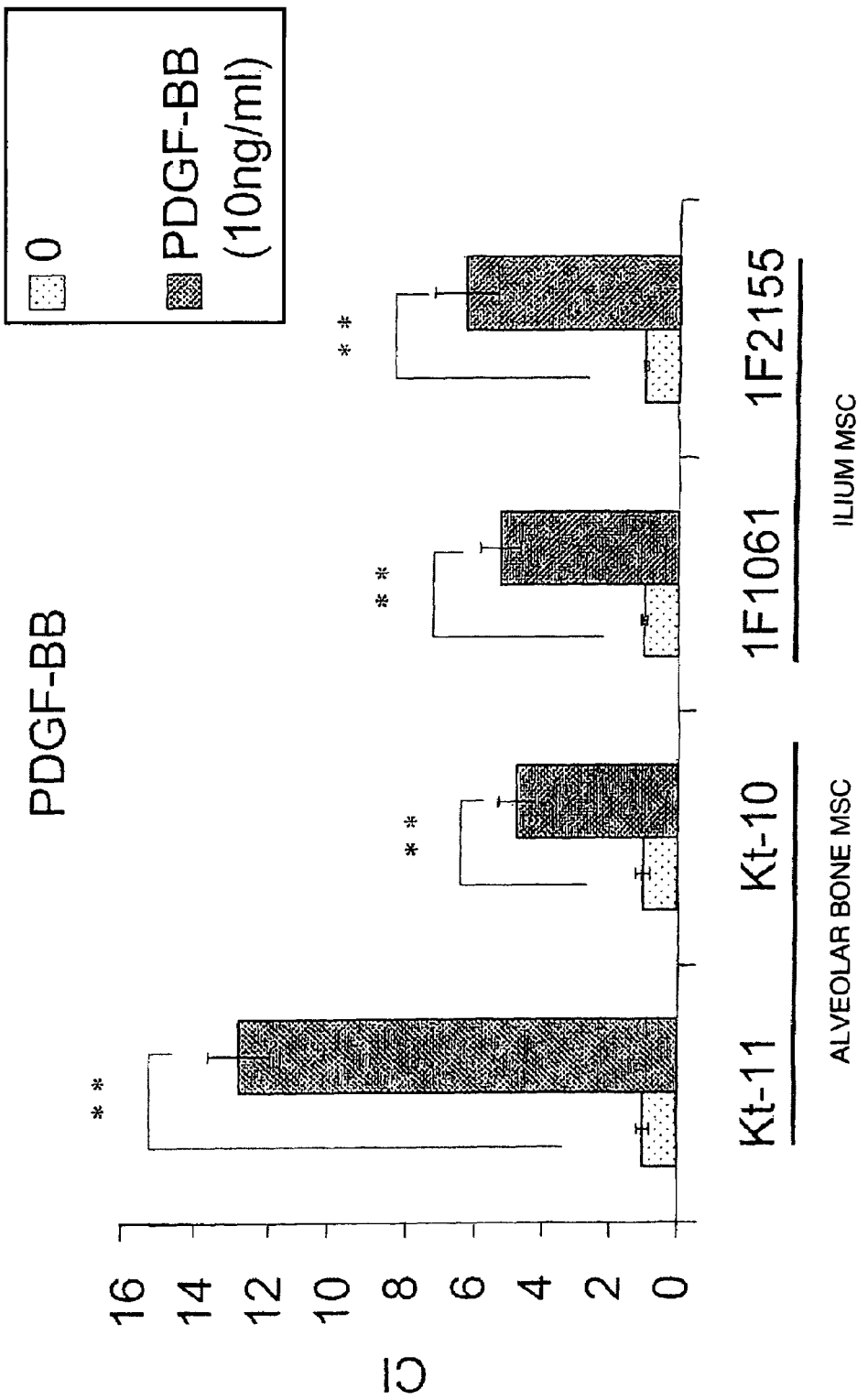
[FIG. 3]
Figure 4:
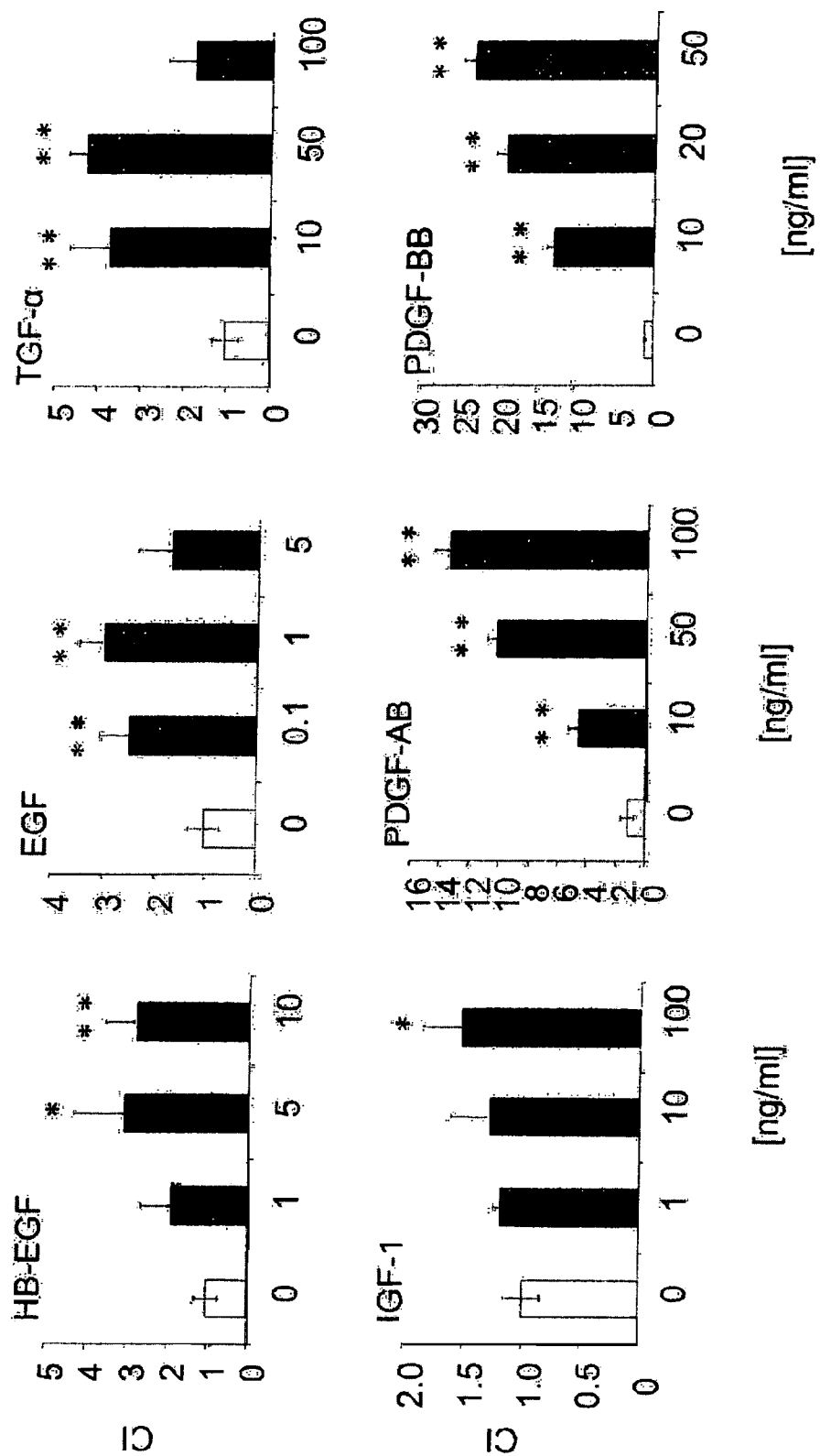
[FIG. 4] The graphs in FIG. 4 show the effects of PDGF-BB, HB-EGF, TGF-α, PDGF-AB, IGF-I and EGF, respectively, at various concentrations in stimulating the migration and accumulation of human-derived MSCs (Kt-11).

FIG. 3 shows the results of PDGF-BB (final concentration: 10 ng/ml) with respect to 1F1061 cells, 1F2155 cells, Kt-10 cells and Kt-11 cells. FIG. 4 shows the effects of HB-EGF, EGF, TGF-α, IGF-I, PDGF-AB and PDGF-BB at various concentrations in stimulating the migration and accumulation of the human-derived MSCs with respect to KT-11 cells. In each of the graphs in FIGS. 3 and 4, * represents p<0.05 and ** represents <0.01, and the vertical bars represent mean±SD.

As is clear from the respective graphs, each of HB-EGF, EGF, TGF-α, IGF-I, PDGF-AB and PDGF-BB significantly enhanced the migration and accumulation of the human-derived MSCs.

Example 3

(Cell Proliferation Test)

The following 20 test substances were evaluated for their effect of stimulating the proliferation of the rabbit-derived MSCs prepared in Example 1: PDGF-BB (product of Genzyme Techne), bFGF (basic fibroblast growth factor, product of KAKEN PHARMACEUTICAL CO., LTD.), HB-EGF (product of Sigma), TGF-α (product of DIACLONE Research), PDGF-AB (product of Genzyme Techne), IGF-I (insulin-like growth factor-I, product of BD Biosciences), EGF (product of Pepro Tech EC), α-thrombin (product of Enzyme Research Laboratories), HGF (product of Pepro Tech EC), PDGF-AA (product of Pepro Tech EC), TGF-β1 (product of Pepro Tech EC), TGF-β3 (product of Pepro Tech EC), IL-2 (product of Pepro Tech EC), SCGF-α (stem cell growth factor-α, product of Pepro Tech EC), SCF (stem cell factor, product of Pepro Tech EC), SDF-1α (stromal cell-derived factor-1α, product of Pepro Tech EC), leptin (product of DIACLONE Research), BDNF (brain-derived neurotrophic factor, product of Wako Pure Chemical Industries, Ltd.), NGF-β (nerve growth factor-β, product of Sigma), and ANP (product of Biogenesis).

The rabbit-derived MSCs were conditioned in a 5% FCS containing Dulbecco's modified Eagle medium and sown on a 96-well TC plate to give a cell density of 3000 cells/well. 24 hours later, the concentration of serum was lowered to 1% and additional 14 hours later, the medium was changed to a serum-free Dulbecco's modified Eagle medium. Following a 10-hour culture in the serum-free medium, the medium was changed to a Dulbecco's modified Eagle medium with which a test substance was diluted to a final concentration of 100 ng/ml. 18 hours later, $^3$H-thymidine was added to give a final concentration of 5 μCi/ml (0.5 μCi/well) and labeling was conducted for 6 hours. The quantity of $^3$H-thymidine absorbed by the labelled cells was measured with a scintillation counter to calculate the percent growth of MSCs. In Table 1, the relative values of $^3$H-thymidine uptake (DPM) in the case of adding the respective factors are shown as the percentage of the control (the numerals following ± represent standard deviation).

Table 1

TABLE 1

| Factor | % control of DPM |
| --- | --- |
| PDGF-BB | 1312 ± 172 |
| bFGF | 809 ± 130 |
| HB-EGF | 591 ± 93 |
| TGF-α | 625 ± 164 |
| PDGF-AB | 762 ± 168 |
| IGF-I | 301 ± 132 |
| EGF | 570 ± 53 |
| α-thrombin | 164 ± 7 |
| HGF | 214 ± 1 |
| PDGF-AA | 101 ± 21 |
| TGF-β1 | 11 ± 6 |
| TGF-β3 | 13 ± 5 |
| IL-2 | 60 ± 26 |
| SCGF-α | 109 ± 25 |
| SCF | 49 ± 8 |
| SDF1-α | 64 ± 24 |
| Leptin | 62 ± 9 |
| BDNF | 90 ± 20 |
| NGF-β | 89 ± 19 |
| ANP | 72 ± 38 |

(Results)

The factors that enhanced the migration of the rabbit-derived MSCs (PDGF-BB, bFGF, HB-EGF, TGF-α, PDGF-AB, IGF-I, EGF, α-thrombin, and HGF) were all effective in enhancing the proliferation of the rabbit-derived MSCs. On the other hand, the factors that had no effect on the migration of the rabbit-derived MSCs (PDGF-AA, TGF-β1, TGF-β3, IL-2, SCGF-α, SCF, SDF-1α, leptin, BDNF, NGF-β, and ANP) were all found to be incapable of significantly enhancing the proliferation of the rabbit-derived MSCS.

Example 4

Using GFP (green fluorescent protein) transgenic rats, a test was conducted to evaluate the in vivo migration of MSCS (GFP-MSCs).

(Cell Cultivation)

GFP-MSCs were isolated from the GFP transgenic rats by the following procedure. The rats were administered intraperitoneally with an excess amount of the anesthetic nembutal, slaughtered, had the thigh bone and the shank removed from both sides, and also had their epiphyses cut off; the bone marrow present in those bones was flushed out using 21-G needles (TERUMO) in about 20 mL, per bone, with Dulbecco's modified Eagle medium (Sigma) (containing penicillin G at a final concentration of 100 units/mL, streptomycin sulfate at a final concentration of 100 μg/mL, amphotericin B (GIBCO) at a final concentration of 0.0085%, and 10% fetal calf serum) and the suspension was separated into individual bone marrow cells using a pipette. A Petri dish (175 cm$^2$; Falcon) containing the above-described Dulbecco's modified Eagle medium was sown with all bone marrow fluid in the thigh bone and the shank for one leg and the cells (MSCs) adhering to the bottom of the dish were kept cultured in the same medium (37° C., 5% $CO_2$, 95% air); when a colony formed (on day 7), the cells were subcultured on a new Petri dish at a cell density of 5000 cells/cm$^2$ and used in the following experiment.

(Transplant Experiment)

Nontransgenic SD rats (n=2) were subjected to general anesthesia with nembutal (i.p. 40 mg/kg), shaven in the right and left calves, and administered by hypodermic injection with 300 μl of 2% atelocollagen containing 1 μg/ml of PDGF-BB. Immediately after that, GFP-MSCs (2×10$^6$ cells/ml, 150 μl) were injected into the tail vein. The control group was administered by hypodermic injection with only PDGF-BB free 2% atelocollagen in an amount of 300 μl.

(Method of Evaluating Migration)

7 days later, muscle and skin tissues of the calves inclusive of the sites into which the collagen was injected were sampled and the total RNA of the cells in the tissues was collected. To be more specific, the total RNA was purified by TRI Reagent (registered trademark of Sigma) and RNeasy (registered trademark) mini kit (QIAGEN). From 2 μg of the total RNA, cDNA was prepared using Omniscript RT (QIAGEN) and GAPDH (housekeeping gene) as well as GFP were subjected to PCR using their specific primers; for GAPDH, 1 μl of a cDNA solution was used as a template whereas 4 μl of a cDNA solution was used as a template for GFP; the PCR was conducted 18 cycles for GAPDH and 40 cycles for GFP, respectively. The resulting PCR products were electrophoresed in a 4% NuSieve (registered trademark) GTG (registered trademark) agarose gel (BMA), stained with ethidium bromide and visualized under UV. The PCR product of GFP appeared as bands corresponding to 129 bp whereas the PCR product of GAPDH appeared as bands corresponding to 613 bp.

(Results)

Figure 5:
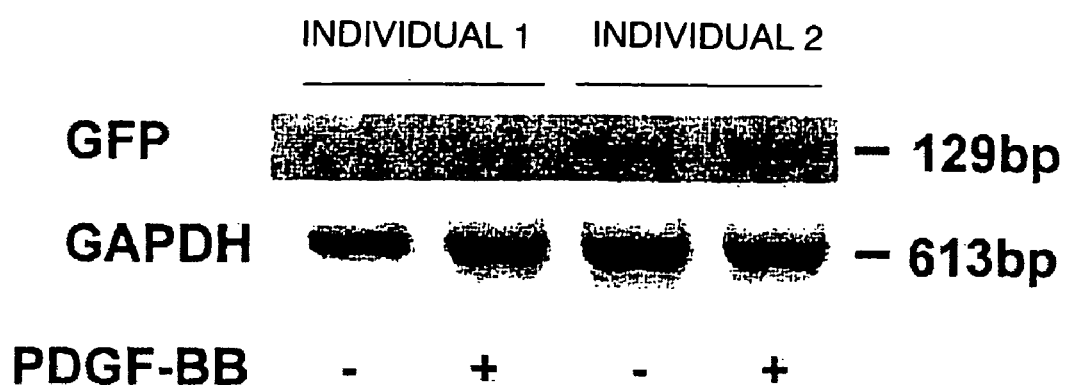
[FIG. 5]
Figure 6:
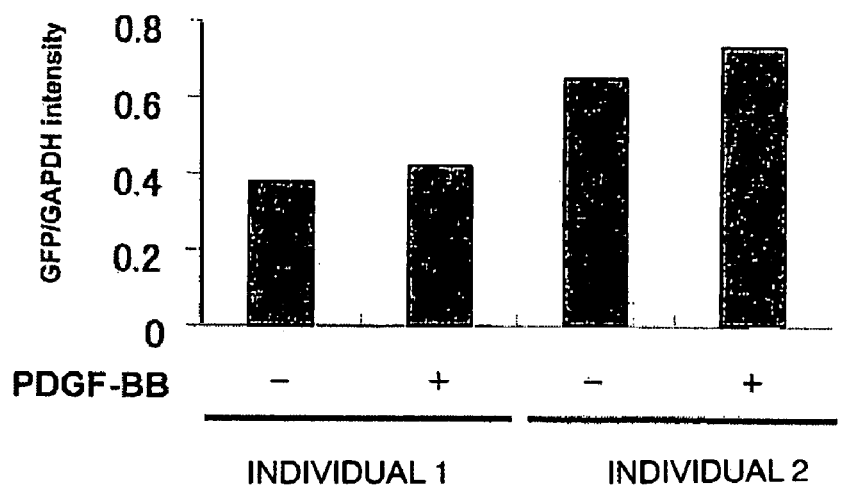
[FIG. 6]

The electrophoretograms in FIG. 5 show the results of RT-PCR performed on the housekeeping gene (GAPDH) and the GFP gene using the total RNA collected from the calves injected with the pure collagen and from the calves injected with the PDGF-BB containing collagen. The presence of the bands corresponding to GFP shows that the GFP-MSCs injected through the tail vein had migrated to the calves. Comparing the amount of GEP RNA between the side injected with the pure collagen (PDGF-BB−) and the side injected with the PDGF-BB containing collagen (PDGF-BB+), one could recognize GFP bands in individual 1 only on the PDGF-BB containing side and in individual 2, one also recognized the stronger band on the PDGF-BB containing side. These bands were scanned and the densities of the GFP bands were corrected with reference to the densities of the respective GAPDH bands; as it turned out, in each of individuals 1 and 2, a larger amount of GFP gene was detected from the calves on the PDGF-BB containing side (FIG. 6). This shows that GFP-MSCS, in the process of their circulating from the tail vein to whole body, migrated and accumulated in greater amounts at the site where PDGF-BB was localized.

INDUSTRIAL APPLICABILITY

The agent, transplant and therapeutic method of the present invention are expected to be useful in regeneration therapy.

The invention claimed is:

1. A method of localizing mesenchymal stem cells to an injury site, which comprises administering to a patient in need thereof mesenchymal stem cells and a mesenchymal stem cell migration-enhancing factor, thereby enhancing the migration and accumulation of the administered mesenchymal stem cells in the injured tissue or suppressing the diffusion of the administered mesenchymal stem cells from the injured tissue to enhance regeneration of the injured tissue, wherein the mesenchymal stem cell migration-enhancing factor is Platelet-Derived Growth Factor-BB (PDGF-BB), wherein the mesenchymal stem cell migration-enhancing factor is administered as a complex with atelocollagen by injection directly into the injured tissue, and wherein the mesenchymal stem cells are administered to the circulatory system.

2. A method of localizing mesenchymal stem cells to an injury site, which comprises administering to a patient in need thereof mesenchymal stem cells and a mesenchymal stem cell migration-enhancing factor, thereby enhancing the migration and accumulation of the administered mesenchymal stem cells in the injured tissue or suppressing the diffusion of the administered mesenchymal stem cells from the injured tissue to enhance regeneration of the injured tissue;

wherein the mesenchymal stem cell migration-enhancing factor is Platelet-Derived Growth Factor-BB (PDGF-BB), and wherein the mesenchymal stem cells are administered to the circulatory system and the mesenchymal stem cell migration-enhancing factor is administered by injection directly to the injured tissue or the periphery thereof.

* * * * *